United States Patent [19]

Wolfe et al.

[11] 4,045,679
[45] Aug. 30, 1977

[54] FLUORESCENT GAS ANALYZER

[75] Inventors: Court Lone Wolfe, Pittsburgh; Ronald Louis Krutz, N. Huntingdon, both of Pa.

[73] Assignee: W. R. Grace & Co., New York, N.Y.

[21] Appl. No.: 690,595

[22] Filed: May 27, 1976

[51] Int. Cl.$^2$ ............................................. G01N 21/38
[52] U.S. Cl. .................................................. 250/461 R
[58] Field of Search ............... 250/252, 365, 372, 373, 250/461 R

[56] References Cited

U.S. PATENT DOCUMENTS

| | | | |
|---|---|---|---|
| 3,795,812 | 3/1974 | Okabe | 250/373 |
| 3,826,920 | 7/1974 | Woodroffe et al. | 250/373 |
| 3,845,309 | 10/1974 | Helm et al. | 250/373 X |

Primary Examiner—Davis L. Willis
Attorney, Agent, or Firm—William Kovensky; Kenneth E. Prince

[57] ABSTRACT

A fluorescent gas analyzer to detect the concentration of a trace gas in another gas or a mixture of gases. The invention is particularly adapted to measure pollutant gases in the air, and still more particularly to measure $SO_2$ in air, stack gases, and the like. The invention includes a removable and heated sample cell. The analytical determinations are made digitally by direct photon counting. The digital logic which handles the data produced by the cell includes means for continuous adjustment to accommodate changes in source energy and means to correct for dark current.

59 Claims, 6 Drawing Figures

FLUORESCENT GAS ANALYZER

It has been known for centuries that certain materials will re-emit light, will fluoresce, when irradiated by a suitable light source. This phenomenon has been used lately in the area of analytical devices for gaseous streams. Such analytical systems, using the fluroescent principle, have many obvious advantages over older methods, such as "wet chemistry". For example, such a device will have a good specific response for sulfur dioxide, be dependable in operation, highly accurate, and can be programmed for a linear response. It will have a low maintenance factor with good response time and will be capable of operation either on the stack or in the control room. Such a device is relatively low in cost when compared to the total cost of other more complex systems.

Included in these advantages is the ability to withstand the severe environments and uses of industrial installations. Further, it is highly desirable that the instrument operate continuously, rather than requiring the presence of an operator to take samples or perform other functions on a regular basis. The present invention was developed specifically to continuously monitor $SO_2$ in air and in stack gases. However, by making suitable adjustments and changes in the source arrangement in the cell, in the sample preparation portion and in the electronics portion, the invention could also be used in a batch type mode, and to measure gases such as NO, $NO_2$, CO, $CO_2$, and others in air, or in other carrier gases. The specific requirement for the gas to be detected is that it be susceptible and be one of the class of gases which will fluoresce when subjected to radiant energy, especially to ultra-violet light.

The term "$SO_2$" as used in the specification and claims herein shall be understood to include all such other gases with which the invention may be used. The specific embodiment described and shown in the drawings is an $SO_2$ analyzer, and that is the reason for the use of the term.

The digital mode of operation of the electronics portion of the invention totally eliminates many of the sources of error in earlier devices. The prior art often integrated the detected fluorescence of the sample cloud in the chamber, which inherently introduces error. Thereafter, this already integrated raw data is often handled in analog type electronics, which, of course, inherently further compounds any error. To make matters still worse, this doubly compounded erroneous result is then often subjected to a statistical sampling technique, a type of analog to digital conversion, which introduces a new third source of error and further compounds the inaccuracies introduced earilier.

In the present invention this kind of sampling, integrating, and the like "smoothing" of the raw data is not used. The invention operates by literally counting the photons of light energy, both the source light and the re-emitted fluorescent light from the irradiated sample. The sampling for reference of the source light as used in the invention is not a statistical type technique. A semi-mirror which will divert and reflect a constant and known portion of the light from the source to the reference pickup is used. Thus, the reference detector "sees" and the electronics is adjusted for operation upon this known and certain amount of light. Other novel means are provided to correct for changes in the source as it ages.

The electronics or data handling portion of the invention operates by digital photon counting. That is, the light re-emitted by the irradiated sample is caused to create electrical pulses, as in a photomultiplier tube, and these pulses are handled directly by the electronics circuitry to produce a digital output. Many prior art circuits operate in an analog mode, which averages data and photon counts, thus introducing error.

The invention includes means interconnecting the sample cell and the electronics portion in such a way that the naturally occurring changes in the source energy are compensated for on a direct basis. That is, it is normal for a U.V. light source to decay in use. The invention measures this and compensates for it in the digital electronics so as to preserve the accuracy of the results produced by the invention instrument over the entire useful life of the source.

Similarly, various other problems inherent in fluorescent analytical devices generally are easily and comfortably accommodated in the digital electronics data handling portion of the invention. These include the corrections for "dark current", and for "stray light" which is a function of the physical configuration of a particular embodiment of the invention. Also, since the data are in digital form initially, they are less susceptible to electrical "noise" from the surroundings than they would be in an analog system.

The invention also includes an improved fluorescent cell and heating means to keep the temperature and the pressure of the sample at a known constant value during analysis. Since the amount of radiation produced is directly proportional to the number of molecules being irradiated, it is important that temperature and pressure be kept constant. Further, the cell of the invention is extremely small and compact, and includes means to readily permit its mounting and dismounting from its enclosure, primarily for cleaning purposes. The cell, heater and their enclosure are so configured as to permit simple machining of the parts without the need for close tolerances.

The analytical portions of analyzers have for many years presented numerous problems which are overcome by this portion of the present invention. Firstly, many such prior sample cells have been permanently mounted. The present invention provides a cell which is readily removable from the device with which it is used, i.e., the cell per se is a separate module. This removability permits easy cleaning, maintenance, replacement of parts, and the like of the cell, which services were heretofore extremely difficult to perform, often requiring substantial amounts of disassembly of the analyzer.

The removable modular cell includes many features which were heretofore present in and around the cell. Certain filters, light traps, lenses, parts of the optical system, flow connections for the sample, and the like, are all built integrally into the cell. A heater mounted in heat conducting contact with the cell to facilitate keeping the sample being irradiated at a known predetermined temperature is included.

The sample cell is mounted in a cabinet or enclosure which includes flow fittings which cooperate with orifices in the cell to connect or disconnect the flow paths to other parts of the analyzer automatically when the cell is moved into or out of position in the enclosure. An arrangement of screws to hold the heating means on the cell, to hold the cell in the enclosure, and to locate and hold the lid on the cabinet in proper position with respect to the cell therein, is provided.

Another aspect is the base member of this enclosure, one end of which is extended and mounts the radiation source thereon. These mounting means have the ability of moving the source in all three degrees of freedom, and to thereafter secure the source in place with respect to the base extension, so that the source, the optics and the cell are in a permanent prefocused factory calibrated arrangement with respect to each other. In this manner, no field adjustment is required and accuracy of results is improved, while use is greatly simplified. The enclosure includes a portion of the optics which are positoned and adjusted between the cell inside the enclosure, and the source without the enclosure to achieve this prefocused arrangement.

The invention provides therefore a dual modular arrangement; the cell proper is mounted in a modular manner within the enclosure. The enclosure, with the cell therein and the source mounted on the extended base member, is also modular with respect to the analyzer. Alternatively, the enclosure can be made large enough to enclose both the cell and the radiation source, which may be desirable depending upon any particular set of requirements.

The above and other advantages of the invention will be pointed out or will become evident in the following detailed description and claims, and in the accompanying drawing also forming a part of the disclosure, in which:

Figure 2:
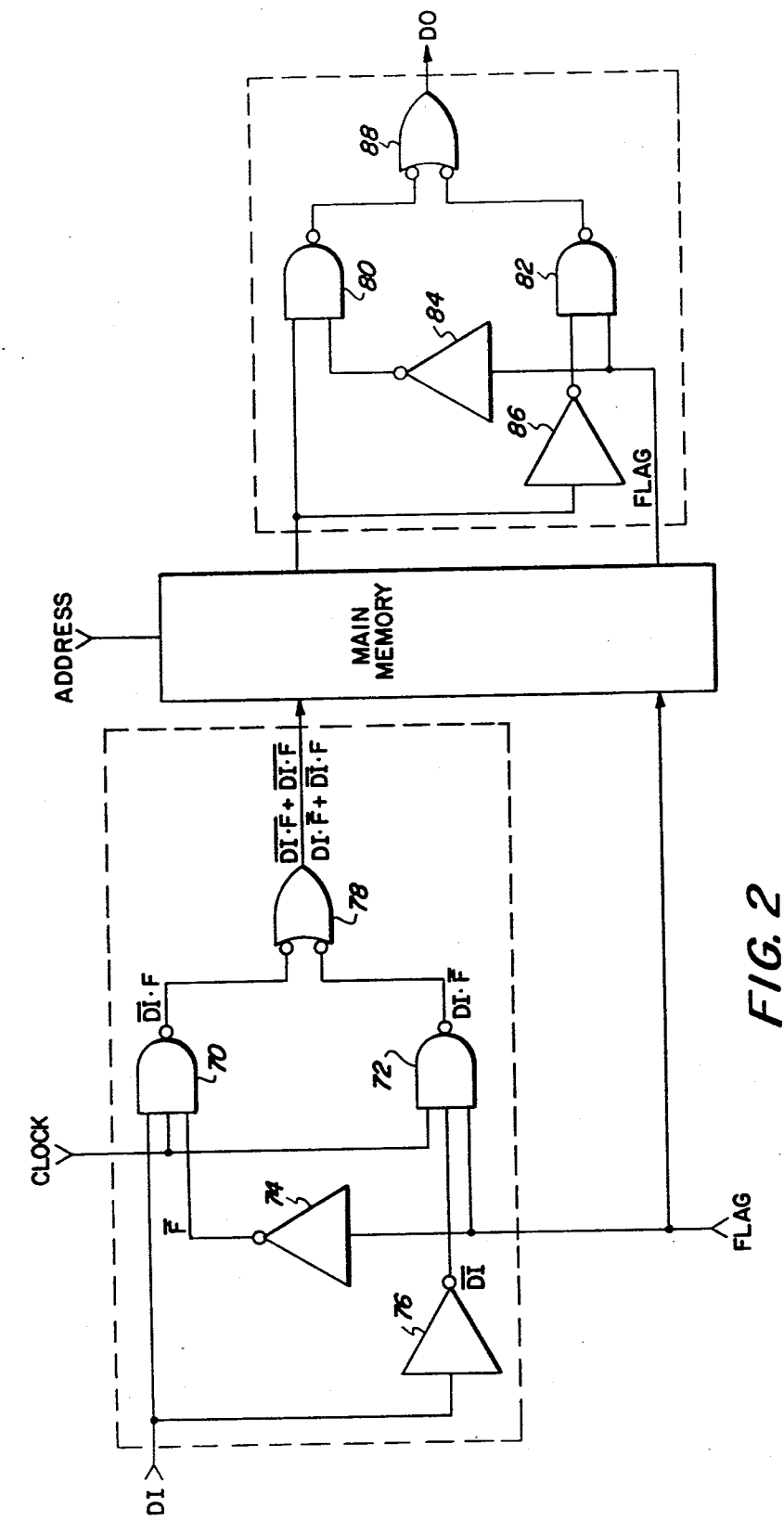
FIG. 2 is a plan view of a preferred form of the invention, with some parts broken away and in cross-section for the sake of clarity.
Figure 3:
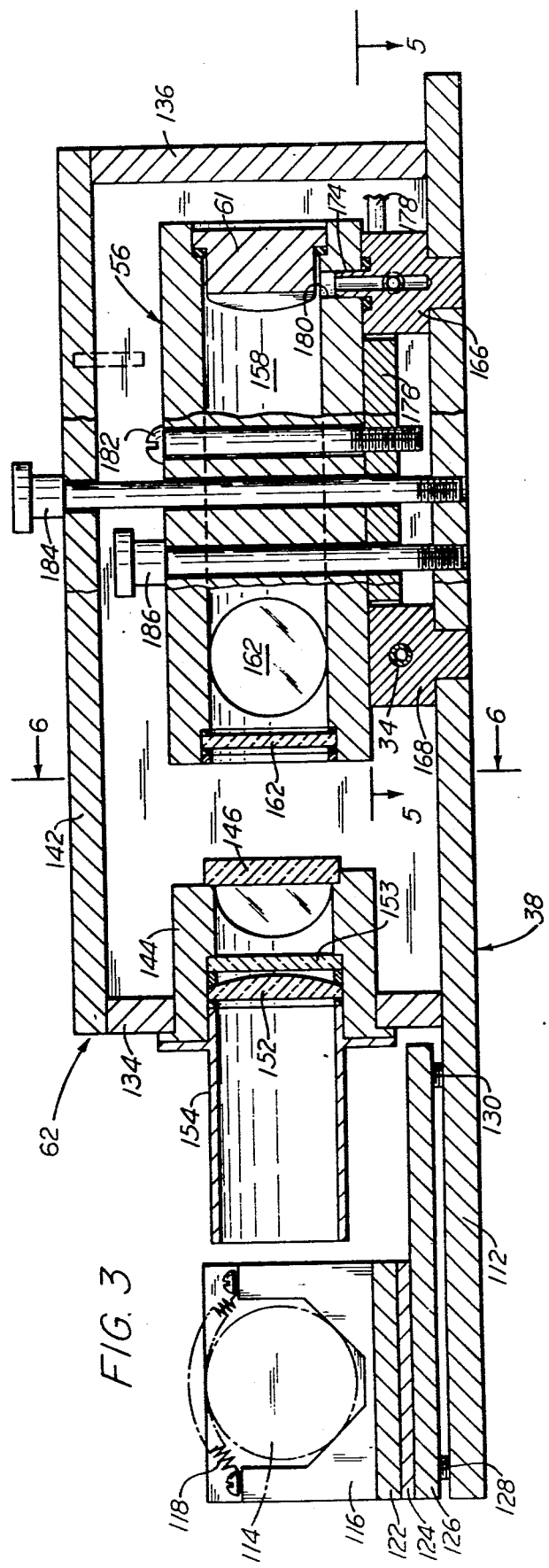
Figure 4:
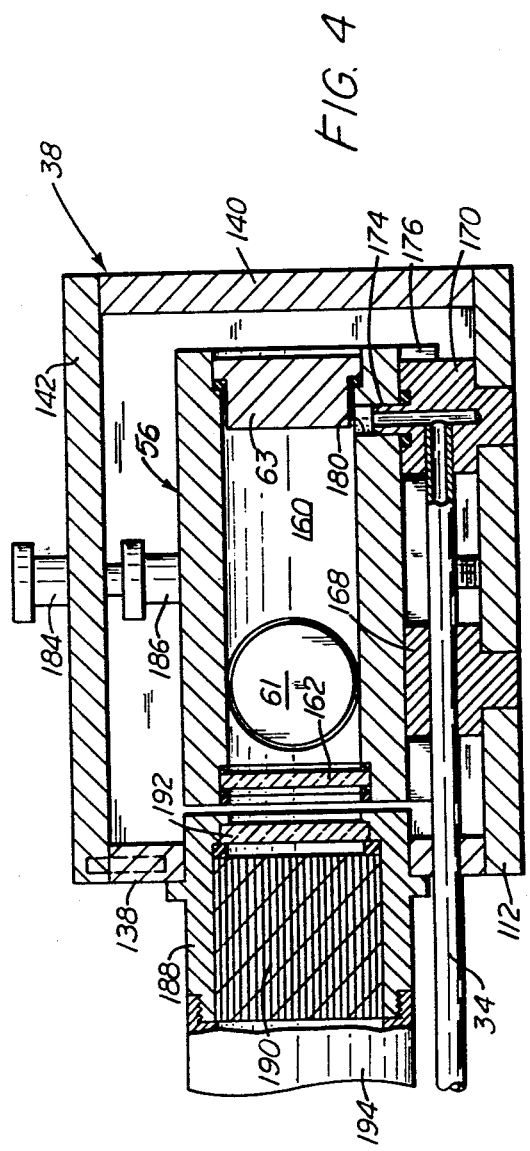
Figure 5:
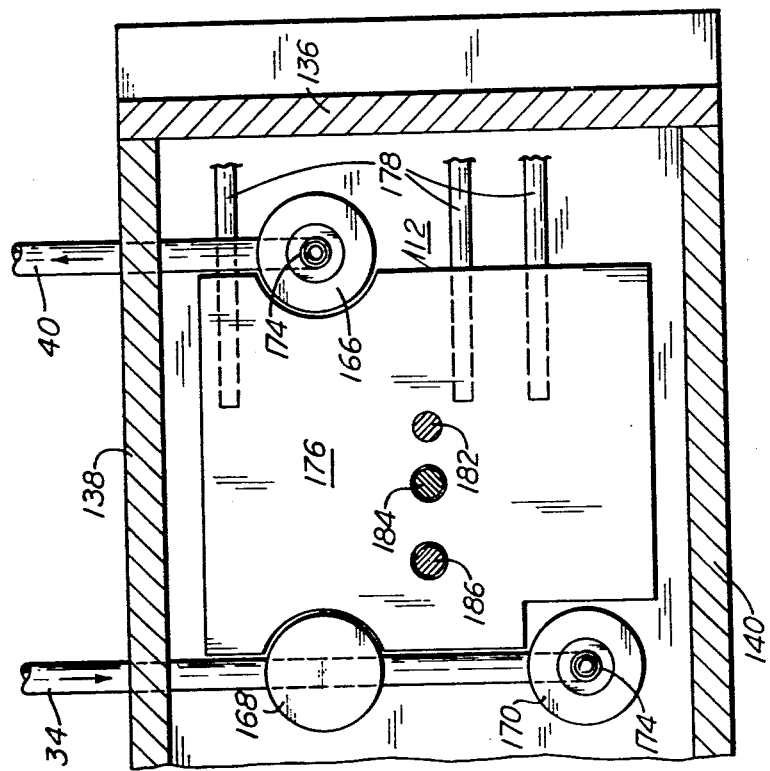
Figure 6:
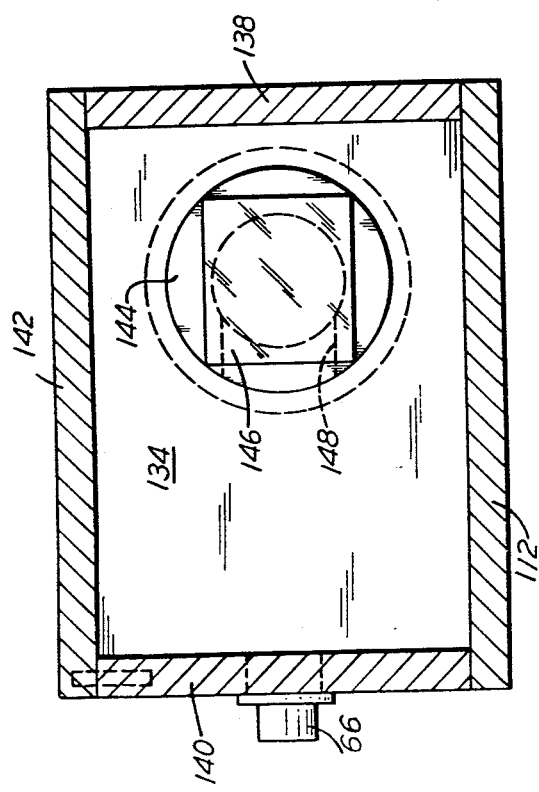
Figure 2:
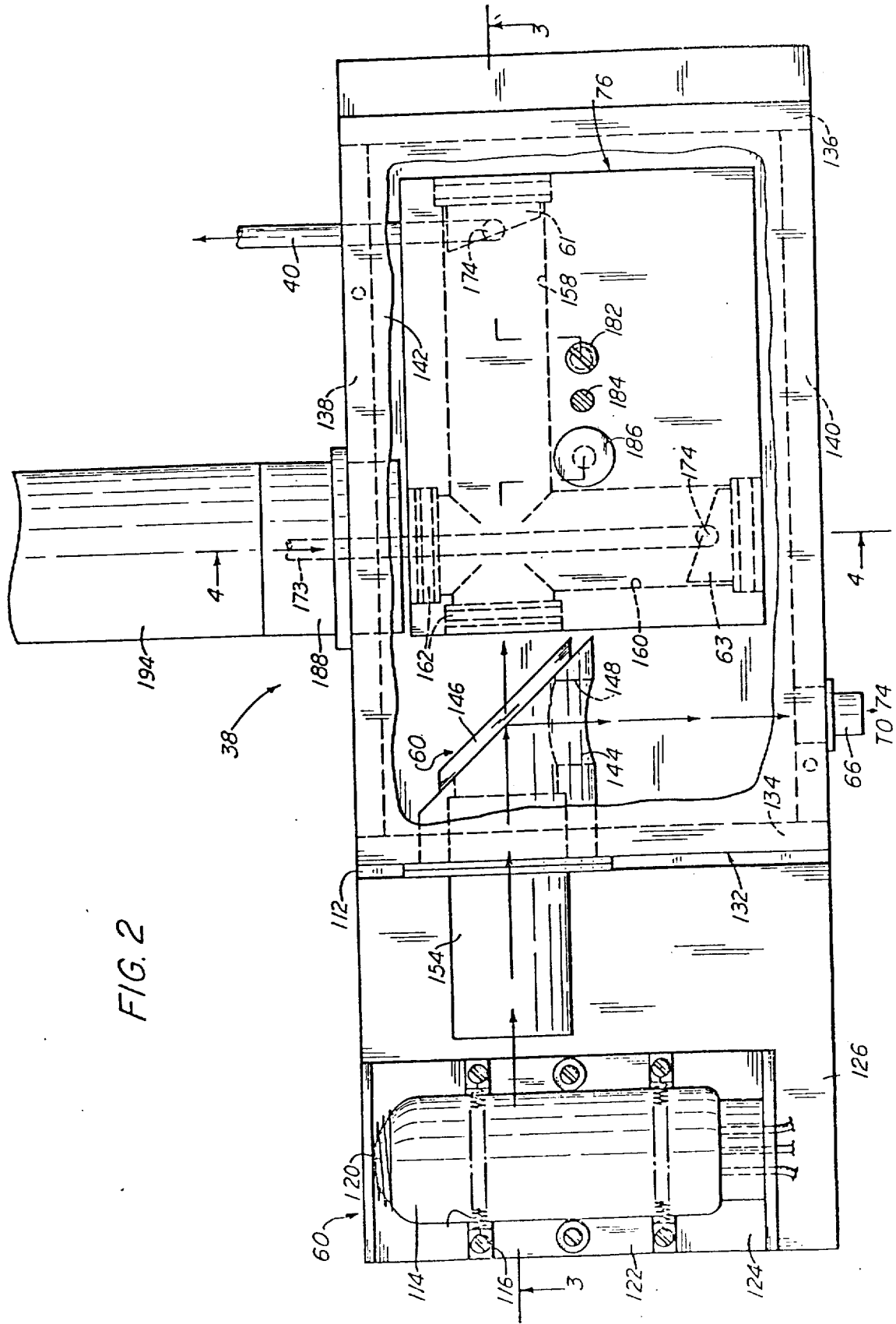

FIGS. 3 and 4 are vertical cross-sectional views taken on lines 3—3 and 4—4 respectively of FIG. 2;

FIG. 5 is a partial plan view taken on line 5—5 of FIG. 3; and FIG. 6 is a vertical cross-sectional view taken on line 6—6 of FIG. 3

Figure 1:
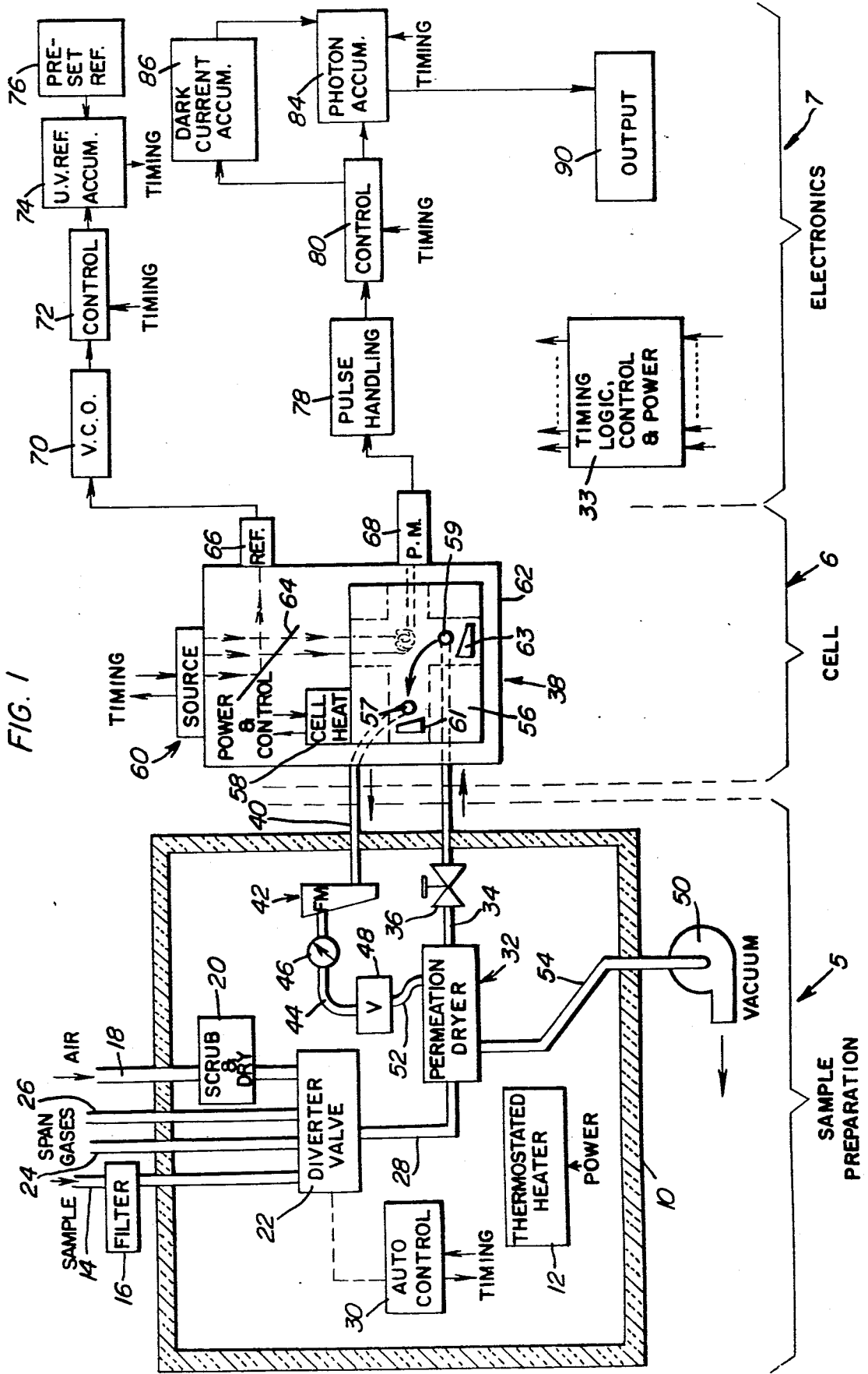
FIG. 1 is a schematic drawing of an embodiment of a fluorescent gas analyzer embodying the invention.

Referring now in detail to FIG. 1 of the drawing, the embodiment of the invention shown comprises three portions, the sample preparation portion 5, the analytical cell portion 6, and the electronics portion 7. The cell and electronics portions, 6 and 7, in the successfully constructed $SO_2$ embodiment of the invention are physically located together in a single module. The sample preparation portion 5 is in a second module, and these two modules together constitute the entire device, together with certain other connections for supplying sample, air for calibration, span gases and the like, as will be set forth in detail below. The double dotted line between portions 5 and 6 indicates the two modules.

Portion 5 is housed in an insulated box 10, which includes a thermostatic heating means 12 to maintain the box and its contents at some predetermined temperature. Controlled power is supplied to this heater as indicated by the arrow. In the successfully constructed embodiment, part 10 was an insulated sturdy metal box which was weather proof and mounted outdoors in close proximity to a smoke stack or flue from which samples were taken for testing.

A line 14, containing a filter 16, passes through a suitably formed sealed opening in the box 10 to deliver sample to the instrument. It is desirable that this line 14 be as short as possible and that the lines be "traced" or heated, in order to maintain the sample in the line delivered to the instrument in a condition as closely approximating the conditions from whence it was taken as possible. That is, if the sample line were allowed to cool excessively, the $SO_2$ content might change due to condensation of water and subsequent absorption of $SO_2$. The filter 16 can be in the line 14 as shown, it could also be within the box 10, or it could be in any other location. What is important is that particulate matter be removed, and that this be done without disturbing the content of the gas of interest in the sample.

Another line 18 delivers air for zeroing through means to scrub and dry the air 20, and thence to a diverter valve means 22. In the successfully constructed embodiment, the scrubbing means 20 includes soda lime which removes all the $SO_2$ in the ambient air supplied through lne 18 so as to properly zero the remainder of the instrument. Any suitable drying means to remove water can also be used in tandem with the scrubbing means. Two different concentrations of span gases are delivered through a pair of lines 24 and 26 to the diverter valve 22. Span gases have predetermined concentration of the gas of interest, and are used, together with the zeroing which is done with pure air delivered from line 18, to properly calibrate the instrument.

Valve means 22 may be of any well-known type to connect only one of the lines 14, 18, 24 and 26 to another line 28. The operation of this valve 22 is controlled by an automatic controller 30, which is in turn controlled from the main overall central timing logic, control means, and power supply of the invention 33.

Block 33 is in electronics portion 7. Various other parts of the invention, such as the power supply to the heater 12, are connected to this "black box" 33, and all such connections are indicated by arrows, which indicated the flow of control, as well as by a suitable word, "timing" or "power", as required. In the successfully constructed embodiment, most of the content of central timing means 33, consisted of a micro-processor suitably programmed to perform many functions throughout the instrument. The micro-processor times the various functions, acquires the data, performs calculations, determines control strategy, sends out control signals, provides display means, takes care of "power-fail" situations, and also does many merely "housekeeping" type functions known to those skilled in these arts as will be set forth as this description progresses.

The use of a micro-processor provides many other advantages to the invention, including flexibility to permit changes in control, linearization and analytical algorithms by changing the "firmware" in the micro-processor rather than by realigning the entire system. Also, self-testing or self cross-checking can be done in the micro-processor's programming, and power failures can be handled "gracefully", i.e. all counters are returned to starting points rather than to random points.

Timing and logic functions can also be performed by automatic timing, or by hybrid circuitry consisting of conventional relays, vacuum tube devices, solid state devices and the like. However, a programmed micro-processor or mini-computer, is the preferred form. In this successfully constructed embodiment, a micro-processor sold by Intel Company of Santa Clara, Calif. their model No. 4040, was successfully used. The device is a four-bit micro-processor which is used with 4702A Read-Only-Memory (ROM) which provides non-volatile program storage, 4002 Random-Access-Memory (RAM) which provides for "scratch pad" data storage, and various other input-out (I/O) chips to form a microcomputer.

The block 30 could also be a manual device to operate the valve 22, or it could be a self-contained timing device to periodically calibrate the remainder of the instrument.

The gas in line 28 passes to a permeation drier 32. In the successfully constructed embodiment, this drier 32 was purchased from Perma-Pure Products of Oceanport, New Jersey. The device is analagous to a shell and tube heat exchanger. The permeable membrane is drawn into fine capillaries which are then formed into a tube bundle. The gas to be dried in line 28 is drawn through a line 34 containing a flow adjusting valve 36, and thence passes on out of box 10 and into the analytical module 38. After going through the sample cell 56 therein, as described below, the sample exits through a line 40, and thence passes through a visual flow meter 42 which serves to allow a quick check that the system is operating normally. The flow meter 42 may be located inside or outside box 10. A line 44 from flow meter 42 contains a pressure gauge 46, and then goes to a back pressure valve 48.

Regulator 48 is an absolute back pressure regulator to keep the pressure constant within the analytical cell, and does so indepentently of filter soiling, barometric pressure, or changes in efficiency of the vacuum pump 50 which controls all of the flow from the diverter valve 22 to this pump 50. The regulator, valve or other means 48 to maintain constant pressure in the cell have been found to improve the results obtained in the invention by precisely controlling the absolute pressure within the sample cell independent of changes in atmospheric pressure. It is highly desirable to maintain a constant pressure within the cell independent of atmospheric variables since the degree of fluorescence is directly a function of the number of molecules intercepted by the irradiating beam and hence directly related to the $SO_2$ concentration in the sample stream. Item 48 could also be two valves arranged to reference to absolute.

After regulator 48, the gas passes through a line 52, through the other side of the drier 32, and thence through a line 54, and is finally exhausted on the output side of the vacuum pump 50. The flows through the drier 32 are counter-current to each other. Moisture is extracted through the permeable membrane capillaries, and is swept out by the vacuum pump 50. In the successfully constructed embodiment, in one installation, an expansion of three to one across the drier at one liter per minute flow rate resulted in a sample dew point of about −30° F.

The permeation drier 32 uses "Nafion" as a permeable membrane. "Nafion" is a DuPont registered trademark for its plastic membrane for general industrial use.

As is well known, $SO_2$ has the proclivity of adsorbing and absorbing on or into or desorbing out of materials in which it is conveyed. Therefore, the selection of materials of construction in portion 5 is important. In the successfully constructed embodiment, all of these tubings were made of either Teflon or stainless steel, and all lengths were kept as short as possible. The sample line 14 is kept free of all control elements, such as diaphram valves and the like, to avoid large unswept volumes which might otherwise permit a harmful effect on the $SO_2$ content of the sample stream.

The span gases and air in the lines 18, 24 and 26 are utilized with conventional techniques to assure that the results produced are accurate. The analytical module 38 includes the analytical cell proper 56, means to heat the cell 58, and a source 60 of radiant energy, preferably U.V., for irradiating the sample in the cell 56.

Inside the enclosure 62 there is provided beam splitter means 64 to direct a known portion of the light from the source 60 to a reference photo detector means 66 (marked REF. in the drawing) mounted on the side of the enclosure 62. The bulk of the energy passes through the beam splitter 64 and impinges upon a window in the cell 56 to irradiate the sample therein, as will be described below.

The invention can be used with other analytical cells. Generally, the invention uses the teaching of U.S. Pat. No. 3,795,812, entitled "Sulfur Dioxide Pollution Monitor", by Hideo Okabe, and assigned to the United States of America. Many different forms of cells in accordance with Okabe's patent could be made and could be used in this invention. Generally, all that is required is that the incident light from the source be at substantially a right angle to the axis of the detector, and that means such as the pair of orifices 57 and 59, be provided to flow sample through the cell. Means are provided to connect the orifices 57 and 59 to the supply and return lines 34 and 40 respectively. Further, light traps are required adjacent the fluorescing cloud of sample gas and at the ends of the lines defined by the incident light from the source and the detector 68. These traps are known and are shown schematically in FIG. 1 at 61 and 63 opposite the detector 68 and the source 60, respectively.

While the invention as shown was designed especially for a continuous flow sample stream containing a gas of interest, such as $SO_2$, in a second carrier gas, such as air; it is also within the scope of the invention to operate upon a single stationary sample. That is, the invention could work in a "batch" type mode as well as in the continuous flowing mode shown.

The housing or enclosure 62 also carries a photomultiplier tube 68, marked P.M., and this device receives the re-emitted energy from the irradiated sample in the cell 56. It is this light picked up by the photomultiplier tube 68 which is proportional to the amount of the gas in question in the carrier gas. That is, the photons detected by the photomultiplier tube 68 are passed into portion 7, and it is this response compared to the output, a solid state reference photo detector 66, which is used to produce an output proportional to the amount of the gas of interest in the carrier gas.

Approximately 4% of the energy from the source was deflected onto the reference detector 66 by the beam splitter. This relatively minor amount is sufficient to provide useful results in portion 7, and is small enough that it has no detrimental effect on the analysis and the results. In this manner detector 66 operates upon a known percentage of the light from source 60, and using this known percentage, the electronics portion 7 is adjusted so as to correct for source decay and to provide a known predetermined amount of light to irradiate the sample in the cell 56, to cause it to fluoresce, as set forth herein.

The preferred form of the source 60 comprised a deuterium lamp, a circuit to turn the lamp on and off in a relatively slow mode of operation, and means to spectrally sort the radiation from the lamp to select that radiation which will cause the gas of interest to fluoresce. Alternatively, the lamp could be left on constantly and a shutter used to get the same result. A model no. L613K deuterium lamp manufactured by Hamamatsu of Japan, having a New York office at Lake Success, New York was successfully used. A circuit built up on a standard circuit was used to operate the lamp in a mode wherein it was on for approximately 30 seconds and then off for approximately 30 seconds. Other means could be used to achieve the same result. For $SO_2$, U. V. radiation in the region of from about 2100 A to about 2300 A is required to cause the $SO_2$ to fluoresce, with the ideal being 2189 A, it fluorescing in turn in the range of about 2400 A to about 4200 A. The source includes suitable filters and windows and the like to accomplish the spectral sorting and the production of energy at the desired wave length, as is well known by those skilled in the art, and as is described in detail below.

If the invention were used to detect a gas other than $SO_2$, such as NO or $CO_2$, then the source spectral sorting, and other portions in the analytical module 38, would be changed appropriately for such other gas to accomodate its fluorescent characteristics.

Referring now to the right hand side of FIG. 1, the voltage from the reference detector 66 is delivered to a voltage controlled oscillator 70, labeled V.C.O. on the drawing. Device 70 produces a train of pulses whose rate per unit time is proportional to the voltage received from the detector 66. The pulses per unit time are in turn proportional to the source intensity and frequency, that is, to the quality of the deuterium lamp in source 60 at the wavelength of interest. The output of the V.C.O. 70 is delivered to a control unit 72, which receives inputs from timing means 33. The controlled output of the V.C.O. 70 is delivered to an accumulating device 74 labeled "U.V. REF. ACCUM.". The output of this accumulator is delivered to the main timing means 33. A preset reference counter 76, labeled "PRE-SET REF.", provides another input to the accumulator 74.

In the successfully constructed embodiment of the invention, the U.V. reference accumulator 74, the preset reference 76, the dark current accumulator 86, and the photon accumulator 84 functions are performed inside the micro-processor chip itself and do not exist as separate physical entities. The drawing, of course, is designed to explain the logic.

The output of the photomultiplier 68 is delivered to pulse handling means 78. These means 78 are by and large conventional including frequency division to be compatible with the micro-processor, and they include a pulse height discriminator and means to shape the pulses, all in a conventional manner, to facilitate the handling of the stream of pulses in the following parts of the circuitry. The thus conditioned pulses are then passed onto a control means 80. Control means 80, via main control 33, passes the pulses coming in from 78 onto photon accumulator 84 either directly or via a dark current accumulator 86. These portions are used in making the dark current correction as is set forth below in the Operation section. Output means 90 receive values from photon accumulator 84 which correspond to the desired final results.

The output means 90 can take many forms, and could include, for example, a digital display, a cathode ray tube display, an analog display, a teletypewriter printout, other such output devices, combinations of such devices, and the like, all well known to those skilled in the art. Further, the output means will include linearizing circuits, suitable latches if a digital output is chosen, various digital to analog converters, and the output can be connected through suitable buffers directly to computers, printers, and the like, if required. The overall operation of the invention including this electronic portion will be set forth in the operation section below.

Referring now to FIGS. 2 to 6, the analytical module 38 and associated parts are shown in detail. The assembly is built upon a base plate 112, which may comprise simply a rectangular flat piece of metal simply machined to mount the other parts thereon.

At its left end, base 112 mounts a radiation source 60, which includes the bulb 114, which is held in a cradle member of assembly 116 by means of hold-down means 118 which may conveniently comprise springs stretched lightly across the top of the bulb or light source and held in place by suitable screws and the like. Depending upon the particular gas being analyzed, the bulb 114 can be of any of several different types. For example, the preferred dueterium lamp, a Zenon lamp of various types, a Zinc, Lead or Antimony source, an RF source, a hydrogen lamp, or any other source emitting electromagnetic radiation of the appropriate wavelength could be used. Shock mounting means in the form of a relatively "soft" large diameter spring 120, can be provided to protect the bulb against shocks.

Means are provided to move the source 60 with respect to base 112 and with respect to the other parts of the invention described below. To this end, a pair of members 122 and 124 are provided, see FIG. 3, for the purpose of adjusting the source in planes parallel to base 112. Further, means are provided to adjust the vertical height of the source on the base. To this end, another base member 126 is mounted on main base 112 by a pair of spring loaded adjustable mounts 128 and 130. The left end mount 128 includes spring means to normally urge the source upwardly with respect to base 112, and the mount 130 at the right end acts like a pivot or a hinge, and includes spring means to load that end of the base 126 downwardly. Mounts 128 and 130 are conventional, and therefore not described or shown in greater detail herein.

To the right of the source assembly, base 112 mounts an enclosure 62 comprising a pair of end walls 134 and 135 interconnected by a pair of side walls 138 and 140, and a lid 142.

The drawings show the preferred embodiment, i.e., the source mounted outside the cell. This arrangement provides the advantage that no additional cooling is required since the heat generated by the source is readily dissipated into the ambient atmosphere. However, there are certain minor concurrent disadvantages to this preferred arrangement; namely, an additional light shield is required to protect the eyes of persons who might be near the equipment, and the possiblity that a careless person could touch a hot source bulb. Thus, it is within the teaching of the invention to make the enclosure, the walls 134 through 140 and the lid 142, large enough to enclose both the source and the cell. This would overcome the above disadvantages, but would generate a need for a fan or other ventilating means to dissipate the heat produced by the source to prevent that heat from adversely affecting the analytical results produced.

In the event both the source and the cell were within an enclosure, the means to direct the energy from the source to the cell, described immediately below, would be mounted, most likely, directly on the base 112, rather than on the enclosure end wall 134. All of such changes are mechanical and easily within the expertise of those skilled in these arts.

Enclosure end wall 134 carries means to direct the energy from the source and to pass it into the inside of the enclosure 62 and the parts therein. The beam collimator, interference filter, and beam splitter assembly 64 is provided for this purpose and it comprises a housing member 144 which is positioned in a suitably formed opening in end wall 134 and mounts a light shield member 154 at its front end. The shape of the housing 144 can be best seen by simultaneously looking at FIGS. 2 and 3. The end of the housing 144 inside the enclosure 134 is cut at about a 45° angle, and it mounts a beam splitter member 146 at its front end. In the successfully constructed embodiment of the invention beam splitter 146 was fabricated from a thin flat disk of high purity quartz which will transmit 98% of the UV energy of interest, and when arranged at a 40° angle to the incident beam will reflect approximately 4% of the radient energy onto the reference detector 66. An opening 148 is formed at right angles to the incident beam so that the reflected reference energy is free to pass out of the supporting means to the reference detector 66.

Rearwardly, to the left in the drawings, of the beam splitter 146, the housing 144 mounts a collimating lens 152 and an interference filter 153 all held in place by suitable O-rings, clamps, screws, and the like, most of which are not shown for the sake of clarity, in the usual manner for fabricating optical devices.

Within the enclosure 134 the invention comprises the analytical cell 56. Cell 56 is basically a rectilinear block of metal with a pair of openings 158 and 160 drilled therethrough at right angles to each other, as is best shown in FIG. 2. Two of the four ends of the two through openings are closed off by quartz window means and the other two by light trap means, as will be set forth in detail below.

The left hand end of the through opening 158, which faces the beam splitter 146, it provided with a quartz window 162, and other suitable means, including O-rings, retaining rings, mounting screws, a source stop, etc., all which are indicated generally and not described herein, and which are conventional in this art. The material of the window 162 however should be selected in conjunction with the wave length of the energy which is desired for purposes of irradiating the sample which will flow through the inside of the cell 56 through the passageways 158 and 160. The left hand end, see FIG. 4, of the other passageway 160, comprises an identical quartz window 162 and associated parts, however, a source stop is not required at this end of passageway 160. The opposite ends of both passageways 158 and 160 are provided with suitable light trap means 61 and 63, such as modified wood light traps, for the purposes of preventing stray light which passes beyond the area of the fluorescent cloud of irradiated sample to reflect back into the photo detector which would have a detrimental effect on results. Further, as is known, it is advantageous to coat all internal surfaces of the cell, i.e. the traps and the sides of the passageways with a black Teflon coating which avoids water collection inside the cell, the black color also serving to dampen stray light.

Means are provided to locate and mount cell 56 in enclosure 132, and also to flow a stream of sample material to, through and out of the passageways 158 and 160 in the cell. To this end, referring to FIG. 5, the base plate 112 carries three mounting and locating pads 166, 168 and 170. The lines 40 and 34 pass through suitably formed and sealed openings in the side wall 138. The supply line 34 passes through a clearance opening in the pad 168, and terminates at the pad 170. The passageway provided in the supply line 173 passes upwardly through pad 170, and terminates in a nozzle portion 174, which is also provided with a suitable seal in the form of an O-ring or the like. In a similar manner, the return line 40 begins from a similar nozzle portion 174 on the pad 166 and thence returns to portion 5. The pads 166, 168 and 170 are similar and each comprises an enlarged central body portion, the bottom shoulder of which rests against the base plate 112, and the upper shoulder of which cooperates with the bottom of the analytical cell 56 to form a seal therewith together with the O-ring or the like in nozzle portion 174. The third pad 178 serves as a support, it does not have a nozzle portion. The enlarged body portions of the three pads are used with the heater, as will be set forth below. Referring to FIG. 5, the heating means 58 comprises a heater block 176 which is formed with a plurality of blind openings in which are mounted conventional heating elements with suitable control means 178.

Thus, referring especially to FIG. 2, it can be seen that the flow of sample is in through the line 34, up through the nozzle 174 at the end of that line in the pad 170, through 160, through the intersection of the passageways 160 and 158 where the cloud of irradiated sample exists, and then through 158 and out through the line 40 via its nozzle portion 174. Vacuum means 50, see FIG. 1, drive this flow. The cell is formed with a pair of openings 180 each adapted to snugly receive a nozzle portion.

Means are provided to hold the heater block 176 up against the underside of the cell 56, to hold the cell 56 with the heater thereon in place on the pads 166, 168 and 170, and to hold the lid 142 down on the enclosure 132. To this end, three screws, 182, 184 and 186 are provided. Each screw has a different predetermined length to perform its particular function, see FIG. 2. The shortest screw 182 fits through a suitably formed clearance opening in the body of the cell 56, and terminates in a mating threaded opening in the body of the heater block 176. The body of the cell 56 is also formed with two other through clearance openings to receive the other two screws 184 and 186. Similarly, the heater block 176 is formed with a pair of through openings which mate with these through openings in the heater block to permit the screws 184 and 186 to pass therethrough. Screw 186 passes through these two registering clearance openings and cooperates with a mating threaded opening in the base 112 to hold cell 56, with or without the heater 176 secured to the underside thereof by its screw 182, down in the enclosure 132 against the three pads 166, 168 and 170. The screws 184 and 186 are provided with enlarged ends to facilitate their use with fingers only. The screw 184 is quite similar to the screw 186, it passes through a clearance opening in the lid 142, and then through two registering clearance openings in the cell 56 and in the heater block 176, finally cooperating with a threaded opening in the base 112. The head of screw 184 holds the lid 142 down on the enclosure to complete the assembly.

As shown in FIG. 5, the heater block 176 is formed with cutouts to mate with and locate against the enlarged body portions of the pads 166 and 168, especially, and with a cutout corner to facilitate manufacture and to clear the third pad 170. In the preferred embodiment, this block 176 was made of aluminum because of its desirable heat transmission qualities. The heater with its control means provides the advantage of holding the cell 56 at any predetermined desired temperature, as dictated by the nature of the material being analyzed, to thereby enhance the results produced with the use of the invention.

Means are provided to take meaningful data through the quartz window at the short end of the through passageway 60, and to deliver said data, or raw observations, to other electronics portion 7. To this end, the side wall 138 is formed with an opening adapted to receive an adaptor member 188. The member 188 is best shown in FIGS. 2 and 4, and it comprises a light trap or light guide 190 which diminishes the effect of internal reflection and the like. At its inner end, in closely spaced position to the window 162, the housing 188 carries another window 192 of the same material as the window 162.

The light guide 190 is a cylindrical section of a product trademarked "Hexacell". In cross section, it is in the form of a honeycomb (nested hexagonal sections) and has the effect of a multiplicity of small diameter, very thin wall parallel tubes nested together as a cylindrical unit. The light guide is blackened to reduce light reflection. It is used to limit the angle of view of the PM tube. At its inner end and closely positioned to the window 162 the housing 188 carries a color filter. The purpose of the color filter is to limit the spectral quality of the light reaching the photo detector 68 to only that emitted by the fluorescent cloud.

At the outer end of the housing 188 there is provided a tubing member 194 which mounts the P.M. 68.

OPERATION

Functioning comprises three parts: (1) settings provided when an invention analyzer is built; (2) corrections and calibrations made prior to use; and (3) operation during normal use.

Initial settings are limited to pre-focusing of the source, and a pre-programmed initial counting time. All other operations are handled in the electronics portion as set forth herein. $SO_2$ free air and span gases are used in the conventional manner to calibrate prior to use of the instrument.

When steady conditions are achieved and the instrument is in normal operation, the sample preparation portion is operating continuously, via the vacuum pump 50. Sample flows from line 14 through valve 22 through the drier 32, through the cell 56, then back through line 40 and to exhaust, passing in heat exchange relationship and drying relationship to its own stream counter-currently through the drier 32. Heater 12 is operating at a predetermined temperature above the dew point of the sample stream. Span gases and calibration air are directed through the cell at regular intervals, manually or automatically, under the control of the electronics portion 7.

Sample flows through the analytical cell 56 while the source, under the control of timing 33, is cycling, that is, the light is going on and off at a rate of approximately 30 seconds on and 30 seconds off. A small part of the light from the source is diverted at 64 and detected at 66 and is then present at the reference accumulator 74, via blocks 70 and 72 as described above. This value is compared to a preset reference value from the device 76. The purpose is to correct for the inherent variance in light output as the lamp ages. This has been a consistently difficult problem to solve in the prior art, and it is very well solved by the digital electronic circuitry of the invention. The correction is accomplished by effectively counting a known portion of the energy emitted from the source on the accumulator 74 and comparing this to a set predetermined number on device 76. This predetermined number corresponds to a predetermined amount of light. Thus, when the bulb is new it may operate only, say, 27 seconds, and later on near the end of its useful life it may stay on for 32 seconds or 33 seconds. The correction is accomplished in that the actual photon light energy is measured and sufficient real time is permitted to elapse to irradiate the sample with a predetermined amount of light regardless of the age and the condition of the source 60. When this predetermined amount of light has irradiated the sample, a timing pulse is delivered to the main timing logic 33 which in turn turns off the source. Simultaneously, with the creation of a value proportional to the accumulation of the reference energy, during each source "on" time, the photo-multiplier tube 68 has been detecting the re-emitted light from the now fluorescing sample in the cell 56. This is the light energy which is proprotional to the content of the gas of interest in the sample stream. The count from P.M. 68 is delivered via the control 80 to accumulator 84 during the source "on" part of the cycle. 84 also incorporates the stray light correction, which, as set forth herein, is proportional to the geometry and the configuration of a particular embodiment of the invention. The control means 80 receives timing inputs from the main timing 33, and is adapted to direct the conditioned pulses detected by the P.M. 68 to either the photon accumulator 84 or the dark current accumulator 86. In the preferred embodiment, all of the above is done internally by "firmware" in the microprocessor chip. The above is set forth to facilitate explanation and understanding.

Then, after the variable length of real time, determined by the production of the predetermined amount of light as set forth above with regard to the elements 66 through 76, has elasped and is "noted" in timing logic 33, the timing means 33 causes 80 to stop passing pulses onto accumulator 84, and this accumulator 84 holds that count. The circuitry counts real time by counting the frequency of the supply voltage, i.e., 60 Hz. This number or value now on accumulator 84 is proportional to the light re-emitted by the irradiated sample cloud in chamber 56, also includes the stray light correction, and also includes the spurious dark current photons which must be substracted to achieve accurate results at output 90. The mirco-processor "notes" when pulses from 66 accumulate up to the reference count and then sends out control pulses.

Timing logic 33 now commences the source "off" portion of the cycle. During this time the dark current photons or pulses generated in the P.M. 68 are actually counted, and this count is stored on the dark current accumulator 86, via control 80. This continues for a length of time equal to the time that the sample was irradiated as determined by parts 66 through 76. The timing logic 33 accomplishes this interaction of the various parts of the circuitry 7.

The drawing shows two accumulators 84 and 86, it being understood, however, that a micro-processor, as opposed to random logic modules was used in the successfully constructed embodiment and that the function of accumulators 74, 76, 80 and 84 are accomplished by the micro-processor. All of the various accumulations, control, generations of values, and the subtraction steps, are, of course, carried out within the micro-processor (or mini-computer) at astronoical speeds, instantaneously by ordinary real time measurement. If separate modules, random logic, were used to build an embodiment of the invention, then it might be desirable to use a single up/down counter in lieu of the two accumulators 84 and 86 with the dark current correction being applied to such a counter in a negative manner. In such event, the "subtraction" would not be performed classically, in a sense of one value being subtracted from another value to produce a third value, but would be performed indirectly; i.e., a positive count being put on the counter and then another count being subtracted from it by being put on the same counter negatively to thereby produce the desired resulting count. The concepts differ slightly, but, considering the nature of the modern solid state electronics being used, the result would be the same.

For this reason, the word "subtracting" and the like as used in the claims herein shall be understood to encompass the function as performed in either the preferred micro-processor, or by random logic, or by other similar means. The important criteria is that the dark current correction value be removed from the total value picked up by the P.M. during the source "on" cycle.

As is known, the dark current phenomenon is a function of temperature, physical configuration of parts, and photomultiplier tube design and construction. It is those spurious photons which are spontaneously generated within the system which are now counted during the source "off" portion of the cycle. The production thereof will continue when the light is turned off, or the shutter closed, and the invention utilizes the fact to substract a value proportional to these spurious pulses which cannot be detected while the light is irradiating sample. By determining the time the light was activated, and counting dark current pulses for the same amount of time, the invention very effectively removes this error to produce accurate results.

It is noteworthy that the invention makes no estimates and uses no preset values but rather makes the dark current correction by actually counting the dark current effect with the same means as are used to count the true data values. This results in a heretofore unobtainable accuracy in making the dark current correction.

Electronics portion 7 also includes means to make the so-called "stray light" correction required in instruments of this type. In this context, "stray light" refers to an inherent characteristic of any particular instrument, namely, the number of spurious pulses any particular embodiment of the invention will pass onto the electronics. This readily accomplished with the use of a device analagous to the reference counter 76 which may be built into or associated with accumulator 84, which is used to, effectively, impress a so-called "zero bias" on the accumulator 84. That is, when each instrument is built, the stray light error is measured and this correction is built into the accumulator 84, and then normally will not be changed during the useful life of that instrument.

While the invention has been described in detail above, it is to be understood that this detailed description is by way of example only, and the protection granted is to be limited only within the spirit of the invention and the scope of the following claims.

We claim:

1. A method of determining the content of a first gas in a gas sample, comprising the steps of irradiating the sample with a predetermined amount of a selected radiant energy to cause the first gas only to fluoresce, measuring the time required to output said predetermined amount of energy, generating a digital value proportional to the fluorescence re-emitted by said irradiated sample while it is being irradiated by said selected radiation using digital counting means, generating a digital dark current correction value by counting pulses proportional to the dark current for a length of time substantially equal to said measured period of time while said gas sample is not being irradiated by said selected radiation, and subtracting the value of the dark current correction from the value of the fluorescence.

2. The method of claim 1, wherein said period of time is measured by comparing a value proportional to a predetermined portion of the radiation to a predetermined value, and then ceasing to irradiate said sample when said last two mentioned values are substantially equal, whereby said measured period of time increases as said source ages and decreases in output.

3. The method of claim 1, and outputting the results of said subtraction step as a value corresponding to said content of said first gas in said sample.

4. The method of claim 3, and operating the method continuously by flowing a stream of sample to the means to cause said first gas to fluoresce while repeatedly performingthe steps to thereby produce a series of said last-mentioned values corresponding to the first gas content.

5. The method of claim 4, and maintaining the sample at a substantially constant pressure while it is being irradiated.

6. The method of claim 1, wherein said first gas is $SO_2$ and said selected energy is U.V. light in the range of about 2100 A to about 2300 A.

7. The method of claim 6, and correcting the value of said re-emitted fluorescence by a predetermined value proportional to the value of the stray light correction for the apparatus used to carry out the method.

8. A gas analyzer comprising an analytical portion comprising a source of radiation selected to cause a selected gas to fluoresce, a cell for containing sample and to premit irradiation of the sample with said radiation, first reference detector means, means to divert a predetermined portion of the source radiation of said reference detector means; second detection means to produce pulses proportional to the fluorescence emitted by the sample while it is being irradiated, means to accumulate a value proportional to the radiation detected by said first detector and means to compare said value to a preset value and to produce a control signal when said values are equal and to determine the amount of time required for said first detector value to equal said preset value, photon accumulator means, means to direct the pulses detected by said second detector to said photon accumulator means while said source is on, dark current accumulator means, means to direct the pulses detected by said second detector to said dark current acccumulator means while said source is off, means to substract the value on said dark current accumulator means generated during a source-off cycle from the value on said photon accumulator means generated during a source-on cycle, and output means to output the difference value produced.

9. The analyzer of claim 8, wherein said gas of interest is $SO_2$ and said selected radiation is U.V. light.

10. The analyzer of claim 8, wherein said source comprises a deuterium lamp and circuit means to operate said lamp on and off for equal periods of time of about 30 seconds each.

11. The analyzer of claim 8, means to flow a sample stream to and through said cell, and means to maintain the pressure of the sample within said cell at a substantially constant predetermined pressure.

12. The analyzer of claim 11, said constant pressure means comprising a back pressure regulator.

13. The analyzer of claim 8, wherein said analytical portion comprises a support member carrying said source, an enclosure for said fluorescent cell mounted on said support member, and heating means for said cell removably mounted in said enclosure and operatively cooperable with said cell to heat said cell to a predetermined temperature.

14. The analyzer of claim 13, wherein said gas of interest is $SO_2$ and said selected radiation is U.V. light, and means to continuously flow a stream of sample through said fluorescent cell.

15. The analyzer of claim 8, wherein said diverting means diverts about 4% of the radiation from said source to said reference detector means.

16. The analyzer of claim 8, said second detection means comprising a photomultiplier tube.

17. The analyzer of claim 16, control means interposed between said photomultiplier tube and said photon and dark current accumulator means; means to direct the pulses from said photomultiplier tube via said control means to said photon accumulator means while said source is on, and means to direct said pulses from said photomultiplier tube via said control means to said second dark current accumulator means while said source is off.

18. The analyzer of claim 8, and a central control and timing means interconnected with and aperating said aforementioned means in a predetermined sequence and for predetermined periods of time.

19. The analyzer of claim 18, said central control and timing means comprising a suitably programmed microprocessor.

20. The analyzer of claim 8, a base member, means to mount said source on said base member, said cell comprising a modular sample cell, means to removably mount said cell on said base member, an enclosure mounted on said base member enclosing at least said cell when it is mounted on said mounting means, means to flow sample to, through and thence out of said cell via said cell mounting means, and means to direct the energy from said source means to said cell.

21. The combination of claim 20, and heating means, means to mount said heating means in contact with said cell, whereby cell and sample therein may be maintained at a predetermined temperature under the control of said heating means.

22. The combination of claim 20, said sample cell comprising a body member of generally rectilinear configuration formed with a pair of fluid flow passageways extending therethrough and intersecting each other at substantially a right angle, said flow means including an inlet in one of said passageways and an outlet in the other of said passageways, whereby sample flows through the intersection of said passageways, window means in at least one of the ends of at least one of said passageways for said energy in closely spaced relation to said intersection, whereby the energy from said source passes from said directing means through said window means to irradiate the sample at said intersection.

23. The combination of claim 20, said enclosure enclosing only said cell, said source means being mounted on a portion of said base member outside said enclosure, and said energy directing means being positioned in a wall of said enclosure between said source means and said cell.

24. The combination of claim 20, said enclosure enclosing said cell and said source means, and said energy directing means being positioned on said base member inside said enclosure between said source means and said cell.

25. The combination of claim 20, said energy directing means comprising beam collimator means and beam splitter means, reference detector means mounted in a wall of said enclosure for receiving a predetermined percentage of the energy from said source from said beam splitter means with the remainder of said energy passing through said beam splitter means to said cell.

26. The combination of claim 20, said cell comprising a body member formed with intersecting fluid flow passageways extending through said body member, window means at an end of each passageway and light trap means at the opposite end of each passageway, heating means for said cell cooperable with said cell mounting means, and means to mount said heating means in contact with said cell.

27. A gas analyzer comprising a source of selected radiant energy, means to turn the source on and off for selected periods of time, means to irradiate a gas sample with a predetermined amount of said radiation to cause the gas of interest in said sample to fluoresce, means to determine the elapsed time required for said source to output said predetermined amount of radiation, means to generate a digital value proportional to the re-emitted fluorescence from the gas of interest, means to generate a digital value proportional to the dark current within said analyzer while said source is off, and means to subtract said value proportional to the dark current from the value of the detected fluorescent light.

28. The analyzer of claim 27, wherein said gas of interest is $SO_2$ and said selected radiant energy is U.V. light.

29. The analyzer of claim 28, wherein said source comprises a deuterium lamp and circuit means to operate said lamp on and off for equal periods of time of about 30 seconds each.

30. The analyzer of claim 27, and means to output the value resulting after said subtraction is performed.

31. The analyzer of claim 28, said irradiation means comprising a fluorescent cell, means to flow a sample stream to and through said cell, and means to maintain the pressure of the sample within said cell at a substantially constant predetermined pressure.

32. The analyzer of claim 31, said constant pressure means comprising a back pressure regulator.

33. The analyzer of claim 27, wherein said means to irradiate comprises an analytical portion comprising a support member carring said source, a fluorescent cell for said sample removably mounted in an enclosure mounted on said support member, and heating means removably mounted in said enclosure and operatively cooperable with said cell.

34. The analyzer of claim 33, wherein said gas of interest is $SO_2$ and said selected radiant energy is U.V. light, and means to continuously flow a stream of sample containing $SO_2$ through said fluorescent cell.

35. The analyzer of claim 27, means to measure said predetermined amount of radiation comprising diverting means interposed between said source and said means to irradiate the sample for diverting a predetermined relatively small portion of the radiation from said source to reference detector means.

36. The analyzer of claim 35, wherein said gas of interest is $SO_2$ and said selected radiant energy is U.V. light, and said diverting means comprising beam splitter means for diverting about 4% of the U.V. light from said source away from said irradiating means.

37. The analyzer of claim 35, said means to measure said predetermined amount of radiation further comprising reference accumulator means, means to input a value corresponding to said predetermined amount of radiation into said reference accumulator means, means to input a value corresponding to said diverted radiation into said reference accumulator means, and means to generate a control signal when said two inputs said reference accumulator means are substantially equal.

38. The analyzer of claim 27, means to detect said re-emitted fluorescence comprising a photomultiplier tube, said means to generate a digital value proportional to re-emitted fluorescence comprising first accumulator means to accumulate the pulses produced by said photomultiplier tube, when said source is on, and said means to generate a value proportional to the dark current comprising second accumulator means connected to said photomultiplier tube while said source is off.

39. The analyzer of claim 38, control means interposed between said photomultiplier tube, and said first and second accumulator means; means to output the value resulting after said subtraction is performed, means to direct the pulses from said photomultiplier tube via said control means to said first accumulator means while said source is on, means to direct said pulses from said photomultiplier tube via said control means to said second dark current accumulator means while said source is off, and means to output the value resulting when the value on said dark current accumulator means is subtracted from the value on said first accumulator means.

40. The analyzer of claim 27, and a central control and timing means interconnected with and for operating all of said aforementioned means in a predetermined sequence and for predetermined periods of time.

41. The analyzer of claim 40, said central control and timing means comprising a suitably programmed microprocessor.

42. The analyzer of claim 27, a base member, means to mount said source on said base member, said means to irradiate comprising modular sample cell, means to removably mount said cell on said base member, an enclosure mounted on said base member enclosing at least said cell when it is mounted on said mounting means, means to flow sample to, through and thence out of said cell via said cell mounting means, and means to direct the energy from said source to said cell.

43. The combination of claim 42, and heating means, means to mount said heating means in contact with said cell, whereby said cell and sample therein may be maintained at a predetermined temperature under the control of said heating means.

44. The combination of claim 42, said sample cell comprising a body member of generally rectilinear configuration formed with a pair of fluid flow passageways extending therethrough and intersecting each other at substantially a right angle, said flow means including an inlet in one of said passageways and an outlet in the other of said passageways, whereby sample flows through the intersection of said passageways, window means in at least one of the ends of at least one of said passageways for said energy in closely spaced relation to said intersection, whereby the energy from said source passes from said directing means through said window means to irradiate the sample at said intersection.

45. The combination of claim 42, said enclosure enclosing only said cell, said source means being mounted on a portion of said base member outside said enclosure, and said energy directing means being positioned in a wall of said enclosure between said source means and said cell.

46. The combination of claim 42, said enclosure enclosing said cell and said source means, and said energy directing means being positioned on said base member inside said enclosure between said source means and said cell.

47. The combination of claim 42, said energy directing means comprising beam collimator means and beam splitter means, reference detector means mounted in a wall of said encloure for receiving a predetermined percentage of the energy from said source from said beam splitter means with the remainder of said energy passing through said beam splitter means to said cell.

48. The combination of claim 42, said cell comprising a body member formed with intersecting fluid flow passageways extending through said body member, window means at an end of each passageway and light trap means at the opposite end of each passageway, heating means for said cell cooperable with said cell mounting means, and means to mount said heating means in contact with said cell.

49. The combination of claim 48, said cell body being of generally rectilinear configuration, said flow means comprising a flow inlet in one of said passageways and a flow outlet in the other of said passageways so positioned that sample will flow therebetween and through the intersection of said passageways, a plurality of mounting pads mounted on said base member to position said cell in predetermined spaced relation to said base member, said flow means further comprising an inlet and an outlet formed in respective ones of said pad members and cooperable with said cell flow inlet and outlet respectively, said heating means comprising a heater block configured to fit in said space between said cell and said base member when said cell is mounted on said pads and said flow means, and said heater block mounting means comprising a screw extending through said cell independently of said passageways therein and having its threaded end cooperating with a mating threaded opening in said heater block, whereby tightening off said screw at the head thereof on one side of said cell draws said heater block against the opposte side of said cell.

50. The combination of claim 49, and means to mount said with or without said heating means connected thereto in said enclosure comprising a screw extending through registering openings in said cell and said heater block when said heater block is mounted on said cell, and said screw comprising a threaded end cooperable with a threaded opening in said base member.

51. The combination of claim 39, and means to secure a lid on said enclosure and to locate said cell with or without said heating means connected thereto in said enclosure comprising a screw mounted in said lid and extending through registering openings in said block, independently of said passageways therein, and said heater block when mounted on said cell, and terminating at a mating threaded opening in said base member.

52. The combination of claim 48 means to mount an energy detection means in a wall of said enclosure in closely spaced relation to a window means in said cell, whereby the fluoresence re-emitted by the irradiated sample at the intersection of said passageways may be detected by means mounted on said energy detection mounting means.

53. The combination of claim 42, said cell being formed with a pair of intersecting passageways, said flow means comprising a pair of openings formed in said cell communicating with said passageways respectively, nozzle means mounted on said base member in positions thereon to communicate with said openings in said cell, and sealing means cooperative with said nozzle means and said openings respectively.

54. A method of determining the content of a first gas in a gas sample, comprising the steps of selecting a radiant energy to cause the first gas only to fluoresce, actuating a source of said selected energy, exposing said sample to a predetermined amount of said selected energy from said source, detecting the fluorescence re-emitted by said irradiated sample, generating a value proportional to the accumulated detected fluorescence, diverting a predetermined portion of the radiation from said source, detecting said diverted source radiation, generating a value proportional to the accumulated detected diverted source radiation, comparing the value of said accumulated diverted radiation to a predetermined value corresponding to said predetermined amount of energy to thereby measure said predetermined amount of energy used to expose said sample; determining a value for the dark current correction by accumulating dark current pulses for a length of time substantially equal to the time said source was activated to produce said predetermined amount of energy; subtracting the value of said accumulated dark current pulses from the value of said accumulated fluorescence, and outputting the value obtained by said subtraction step.

55. The method of claim 54, and correcting the value corresponding to the accumulated detected fluorescence with a constant value corresponding to the stray light correction for the particular apparatus being used to carry out the steps of the method.

56. The method of claim 54, and continuously flowing a stream of said sample gases from a source of said first gas to and through the means for exposing the sample to the selected energy.

57. The method of claim 56, and maintaining the sample at a substantially constant pressure while it is in said means for exposing.

58. The method of claim 54, wherein said first gas is $SO_2$ and said selected radiant energy is U.V. light in the range of about 2100 A to about 2300 A.

59. The method of claim 58, and correcting the value of said re-emitted fluorescence by a predetermined value proportional to the value of the stray light correction for the apparatus used to carry out the method.

* * * * *

UNITED STATES PATENT AND TRADEMARK OFFICE
CERTIFICATE OF CORRECTION

PATENT NO. : 4,045,679

DATED : August 30, 1977

INVENTOR(S) : Court Lone Wolfe and Ronald Louis Krutz

It is certified that error appears in the above-identified patent and that said Letters Patent are hereby corrected as shown below:

Claim 8, line 6, after "radiation" delete "of" and insert --to--.

Claim 18, line 2, change "aperating" to --operating--.

Claim 37, line 8, change "two inputs said" to read -- two inputs into said--.

Claim 42, line 3, after "comprising" insert --a--.

Claim 50, line 2, change "said with" to read --said cell with--.

Claim 51, line 1, change the dependency from "39" to --49--.

UNITED STATES PATENT AND TRADEMARK OFFICE
CERTIFICATE OF CORRECTION

PATENT NO. : 4,045,679

DATED : August 30, 1977

INVENTOR(S) : Court L. Wolfe and Ronald L. Krutz

It is certified that error appears in the above-identified patent and that said Letters Patent are hereby corrected as shown below:

Delete sheet 2 of the drawing figures and insert the correct page attached hereto.

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*